(12) United States Patent
Zheng et al.

(10) Patent No.: US 12,307,569 B2
(45) Date of Patent: May 20, 2025

(54) GPU-BASED INTEGRATED PROCESSING METHOD AND SYSTEM FOR GEOCHEMICAL DATA

(71) Applicants: China University of Geosciences (Beijing), Beijing (CN); Tibet Julong Copper Co., Ltd., Lhasa (CN)

(72) Inventors: Youye Zheng, Beijing (CN); Zhaolong Xue, Beijing (CN); Jiancuo Luosang, Lhasa (CN); Jiangang Wei, Lhasa (CN); Jingjing Li, Lhasa (CN); Peng Kang, Lhasa (CN); Zhuoga Suolang, Lhasa (CN)

(73) Assignees: China University of Geosciences (Beijing), Beijing (CN); Tibet Julong Copper Co., Ltd., Lhasa (CN)

( * ) Notice: Subject to any disclaimer, the term of this patent is extended or adjusted under 35 U.S.C. 154(b) by 0 days.

(21) Appl. No.: 18/596,686

(22) Filed: Mar. 6, 2024

(65) Prior Publication Data
US 2024/0303901 A1  Sep. 12, 2024

(30) Foreign Application Priority Data
Mar. 8, 2023 (CN) .......................... 202310239808.4

(51) Int. Cl.
  G06T 15/00 (2011.01)
  G06T 19/20 (2011.01)
(52) U.S. Cl.
  CPC ............ *G06T 15/005* (2013.01); *G06T 19/20* (2013.01); *G06T 2219/2012* (2013.01)

(58) Field of Classification Search
  None
  See application file for complete search history.

(56) References Cited

U.S. PATENT DOCUMENTS

| 11,385,214 | B2 * | 7/2022 | Michael ................. G01N 33/24 |
| 2008/0288173 | A1 | 11/2008 | Saenger | |
| 2017/0358129 | A1 | 12/2017 | Chen et al. | |
| 2018/0328905 | A1 * | 11/2018 | Jacobi ................. G01N 23/2251 |
| 2020/0191943 | A1 | 6/2020 | Wu et al. | |

\* cited by examiner

*Primary Examiner* — Andrew G Yang
(74) *Attorney, Agent, or Firm* — True Shepherd LLC; Andrew C. Cheng

(57) ABSTRACT

A GPU-based integrated processing method for geochemical data, includes the following steps: S1, storing geochemical data in a format of a preset three-dimensional array data structure Struct_A, S2, iteratively processing the formatted geochemical data by using a compute shader in a GPU, calculating a mean value and a standard deviation of content of each chemical element, calculating a threshold value of the chemical element, eliminating sampling points according to the threshold value, repeating the operations until there is no sampling point to be eliminated, and calculating a final mean value as a background value and a final threshold value as a lower limit value of anomaly; and S3, constructing spatial coordinates according to the obtained new geochemical data set, loading the spatial coordinates into a fragment shader for rendering, and completing anomaly delineation according to the background value and the lower limit value of anomaly.

8 Claims, 8 Drawing Sheets

3.1 Construct a Vertex using data from $CSet_2$, where spatial coordinates are used as vertex coordinates and chemical element values are used as vertex attributes (GLSL attributes, or other equivalent methods)

↓

3.2 Triangulate $CSet_2$ in any method, to generate a list of vertex numbers for triangle drawing, where in this process, data interpolation can be performed to obtain a smoother anomaly map

↓

3.3 Dispatch a fragment shader program, transmit the background value PMN and the lower limit value PtN of anomaly obtained in step 2.5 in a uniform form, and dispatch the fragment shader program

↓

3.3.1 Define an anomalous color of a chemical element as C1 and a non-anomalous color as C2; for each pixel of the chemical element, if the value of the chemical element in the pixel attribute is greater than PMN or PtN, set the pixel color as C1; otherwise, set the pixel color as C2

↓

3.3.2 Select a color mixing method for a multi-element anomaly map according to actual situations

↓

3.4 Complete anomaly delineation

FIG. 6

GPU-BASED INTEGRATED PROCESSING METHOD AND SYSTEM FOR GEOCHEMICAL DATA

CROSS-REFERENCE TO RELATED APPLICATIONS

This application claims priority to Chinese Patent Application No. 202310239808.4 with a filing date of Mar. 8, 2023. The content of the aforementioned application, including any intervening amendments thereto, is incorporated herein by reference.

TECHNICAL FIELD

The present disclosure relates to the technical field of geochemical exploration, and in particular to a graphics processing unit (GPU)-based integrated processing method and system for geochemical data.

BACKGROUND

Geochemical exploration is a critical component of ore prospecting, and the processing of geochemical data is a key aspect of this exploration. Geochemical data processing refers to the processing, analysis and interpretation of geochemical data in order to extract information that is of geological prospecting significance, as well as other useful information in the field of geochemical exploration and research. Typically, statistical tools are used to filter the collected sample data, identify anomalous sample points, and delineate the anomaly range to create an anomaly map. The areas displaying anomalies indicate the potential for ore prospecting.

After the integration of computer technology into ore prospecting, geochemical data processing has made significant advancements. The utilization of high-speed computer processing has allowed for the application of various complex statistical methods in geochemical data processing, such as cluster analysis, factor analysis, and discriminant analysis.

With the continuous development of computer technology, more advanced data processing methods are being utilized in geochemical data processing. For instance, Shi Changyi et al. introduced the "subregion median contrast filtering method" in 1999, Cheng Qiuming proposed the local singularity theory in 2001, and Han Dongyu et al. combined fractal theory to suggest the "content-total method for determining the lower limit of anomaly" and the "fractal trend surface method" in 2004.

Nowadays, artificial intelligence and machine learning technology are being utilized in geochemical data processing.

Once the processing is finalized, it is crucial to generate an anomaly map based on the data results and delineate the boundaries of the anomalous region. Currently, the delineation of anomalous regions typically involves human-computer interaction using software such as Surfer and MapGIS.

In practical applications, geochemical data processing is commonly performed iteratively with Excel. The specific principle of the iterative method is as follows: Firstly, the mean value $X_1$ and standard deviation $Sd_1$ of the content values of the element are calculated, and then all values larger than $X_1+n \times Sd_1$ are removed to obtain a new data set; the mean value $X_2$ and standard deviation $Sd_2$ of the new data set are calculated, and then all values larger than $X_2+n \times Sd_2$ are removed; the above operations are repeated until there are no values to be removed. n is 2 or 3. The final mean value $X_i$ is the background value, and $X_i+2 \times Sd_n$ is the lower limit of anomaly. In practical applications, if the element content value at a sampling point isn't within the range between the background value and the lower limit of anomaly, the sampling point is considered as an anomalous region.

Excel is commonly used for manual calculations to determine the background value and anomalous value in practice. However, it is a great challenge to use Excel for processing a large amount of data, such as 40 types of elements at 100,000 sampling points. Once the processing is finished, the data is typically imported into software such as Surfer or MapGIS, where colors are assigned based on the value of each point, to generate an anomaly map. These processes often involve significant manual intervention and effort. In order to improve the processing efficiency, data processing tools, such as Geochem Studio, have appeared, which can conveniently import and process geochemical data as required, and draw the anomaly map, simplifying the operation process.

Compared with manual operations, existing automatic processing tools offer improved efficiency. However, if the resulting map does not meet expectations, the entire process needs be repeated to adjust the processing parameters. It is currently not possible to modify the parameters in real-time while observing the mapping results. This issue stems from the fact that data processing and drawing are conducted on the central processing unit (CPU) using serial processing. CPUs are naturally not optimized for graphics data processing.

While GPUs are capable of parallel processing, the different hardware architectures of CPUs and GPUs mean that existing computer processing methods can only run on CPUs and cannot simply be transferred to GPUs.

SUMMARY OF PRESENT INVENTION

The purpose of the present disclosure is to provide a GPU-based integrated processing method and system for geochemical data, to accelerate geochemical data processing and anomaly map drawing and achieve real-time interactive delineation of geochemical anomalies; and it is capable of shifting the process of geochemical data processing and anomaly map drawing from CPU to GPU.

The GPU-based integrated processing method for geochemical data according to the present disclosure includes the following steps:

S1: storing geochemical data in a format of a preset three-dimensional array data structure Struct_A, where a first dimension of the three-dimensional array data structure Struct_A represents sampling points, a second dimension represents chemical elements, and a third dimension is used for counting sampling points and storing chemical element values;

S2: iteratively processing the formatted geochemical data by using a compute shader in a GPU, to be specific, performing pairwise parallel iterative addition on adjacent sampling points until an iterative sum of content of each chemical element in all sampling points is calculated, accordingly calculating a mean value and a standard deviation of content of each chemical element, calculating a threshold value of the chemical element, eliminating sampling points having a chemical element content below the threshold value, repeating the operations until there is no sampling point to be eliminated to obtain a new geochemical data set, and calculating a final mean value of the new geochemical data set as a background value and a final threshold value of the new geochemical data set as a lower limit value of anomaly; and S3: constructing spatial coordinates according to the new geochemical data set, loading the spatial coordinates into a fragment shader for rendering, and completing anomaly delineation according to the background value and the lower limit value of anomaly.

According to the above technical solutions, the specific process of the step S2 is as follows:

S21: creating a first buffer and a second buffer accessible to the compute shader, writing an initial geochemical data set $CSet_1$ in the format Struct_A into the first buffer, performing pairwise parallel vector summation on sampling point count values C and chemical element values V of adjacent sampling points, storing results in the second buffer, performing pairwise summation on data in the second buffer and storing results in the first buffer, repeating the operations until a vector sum of sampling point count values C and chemical element values V of all the chemical elements in all the sampling points is calculated, and calculating a mean value PM of each chemical element by determining a ratio of the C to the V;

S22: creating a third buffer and a fourth buffer accessible to the compute shader, writing the initial geochemical data set $CSet_1$ into the third buffer, parallelly calculating a sum of squared differences between the chemical element values V of each chemical element and the corresponding mean value PM in adjacent sampling points and calculating a vector sum of sampling point count values C in adjacent sampling points, storing results in the fourth buffer, performing pairwise parallel summation on adjacent sampling points in the fourth buffer and storing results in the third buffer, repeating the operations until a sum of squared differences between the chemical element values V and PM and a vector sum of the sampling point count values C in all sampling points are calculated, and accordingly calculating a standard deviation PSd of each chemical element; calculating the threshold value according to the mean value PM and the standard deviation PSd, and filtering the initial geochemical data set $CSet_1$ according to the threshold value to obtain a filtered geochemical data set $CSet_2$; and S23: filtering the filtered geochemical data set $CSet_2$ in a same manner until there is no sampling point to be eliminated; and obtaining the final mean value PMN of each chemical element as the background value, and the final threshold value PtN of each chemical element as the lower limit value of anomaly.

In one embodiment, the sampling point count values C of all chemical elements in the initial geochemical data set $CSet_1$ are initialized to 1.

In one embodiment, the sampling point count values C values and the chemical element values V of all chemical elements in the second buffer and the fourth buffer are initialized to 0.

In one embodiment, a memory offset of the first buffer is twice of a memory offset of the second buffer; and a memory offset of the third buffer is twice of a memory of the fourth buffer.

In one embodiment, when a chemical element value of a chemical element in adjacent sampling points is 0, a sampling point count value of the chemical element is also set to 0.

In one embodiment, the specific process of the step S3 specifically includes:

S31: creating a vertex buffer object (VBO) based on the new geochemical data set, where the spatial coordinates are used as vertex coordinates and the chemical element values are used as vertex attributes;

S32: triangulating the new geochemical data set, generating a list of vertex numbers for triangle drawing, and performing data interpolating in the process to obtain a smooth anomaly map to be delineated; and S33: according to the background value PMN and the lower limit value of anomaly PtN, coloring the anomaly graph to be delineated in the fragment shader; when an attribute value of a vertex is greater than the background value PMN or the lower limit value PtN of anomaly, setting a pixel of the vertex as an anomalous color; otherwise, setting the pixel as a non-anomalous color, to complete the anomaly delineation.

In one embodiment, when the anomaly map to be delineated is a multi-chemical element anomaly map, multiple color mixing methods are selected according to actual situations.

The present disclosure further provides a GPU-based integrated processing apparatus for geochemical data, and the apparatus includes:

a three-dimensional array module configured to store geochemical data in a format of a preset three-dimensional array data structure Struct_A, where a first dimension of the three-dimensional array data structure Struct_A represents sampling points, a second dimension represents chemical elements, and a third dimension is used for counting sampling points and storing chemical element values;

a background value calculation module configured to iteratively process the formatted geochemical data by using a compute shader in a GPU, to be specific, perform pairwise parallel iterative addition on adjacent sampling points until an iterative sum of content of each chemical element in all sampling points is calculated, accordingly calculate a mean value and a standard deviation of content of each chemical element, calculate a threshold value of the chemical element, eliminate sampling points having a chemical element content below the threshold value, repeat the operations until there is no sampling point to be eliminated to obtain a new geochemical data set, and calculate a final mean value of the new geochemical data set as a background value and a final threshold value of the new geochemical data set as a lower limit value of anomaly; and an anomaly delineation module configured to construct spatial coordinates according to the new geochemical data set, load the spatial coordinates into a fragment shader for rendering, and complete anomaly delineation according to the background value and the lower limit value of anomaly.

The present disclosure further provides a computer storage medium, the computer storage medium stores a computer program executable by a processor, and the computer program implements the GPU-based integrated processing method for geochemical data according to any one of the above technical solutions.

The present disclosure has the following beneficial effects:

First of all, based on the multi-core advantage of the GPU, the present disclosure can provide strong computing power, and can quickly perform parallel pairwise summation, thus improving the computing efficiency of the present disclosure.

Secondly, the three-dimensional array Struct_A adopted by the present disclosure is constructed according to two basic operational attributes in geochemical data processing. The essence of geochemical data processing is a cycle of three steps, namely, (1) calculating a mean value, (2) calculating a standard deviation, and (3) filtering. Throughout the entire operation, the calculation for each step is realized by reusing the two variables C and V, without defining a dedicated storage mode for each operation, which not only simplifies the program design, but also reduces the overhead of memory copying, thus improving the operation efficiency.

In addition, the present disclosure specifically improves the compute shader for the traditional geochemical data processing method known as the "iteration method". The traditional geochemical data processing involves calculating the mean value, calculating the standard deviation, and filtering the sample geochemical data through iterative steps, to determine regional geochemical background value and lower limit of anomaly, which are used to distinguish which samples are "anomalous values", ultimately aiding in the delineation of potential prospecting regions. Based on the core idea of iterative method and the traditional calculation method, the present disclosure adapts parallel processing, to achieve the same results on the GPU as on the CPU, such that the processing speed is greatly improved and the user experience is improved.

BRIEF DESCRIPTION OF THE DRAWINGS

FIG. 6 is a schematic flowchart showing a step 3 in a GPU-based integrated processing method for geochemical data according to the present disclosure;

DETAILED DESCRIPTION OF THE EMBODIMENTS

The present disclosure is further described in detail below with reference to the accompanying drawings and specific examples, but the embodiments shall not be construed as a limitation to the present disclosure.

Figure 1:
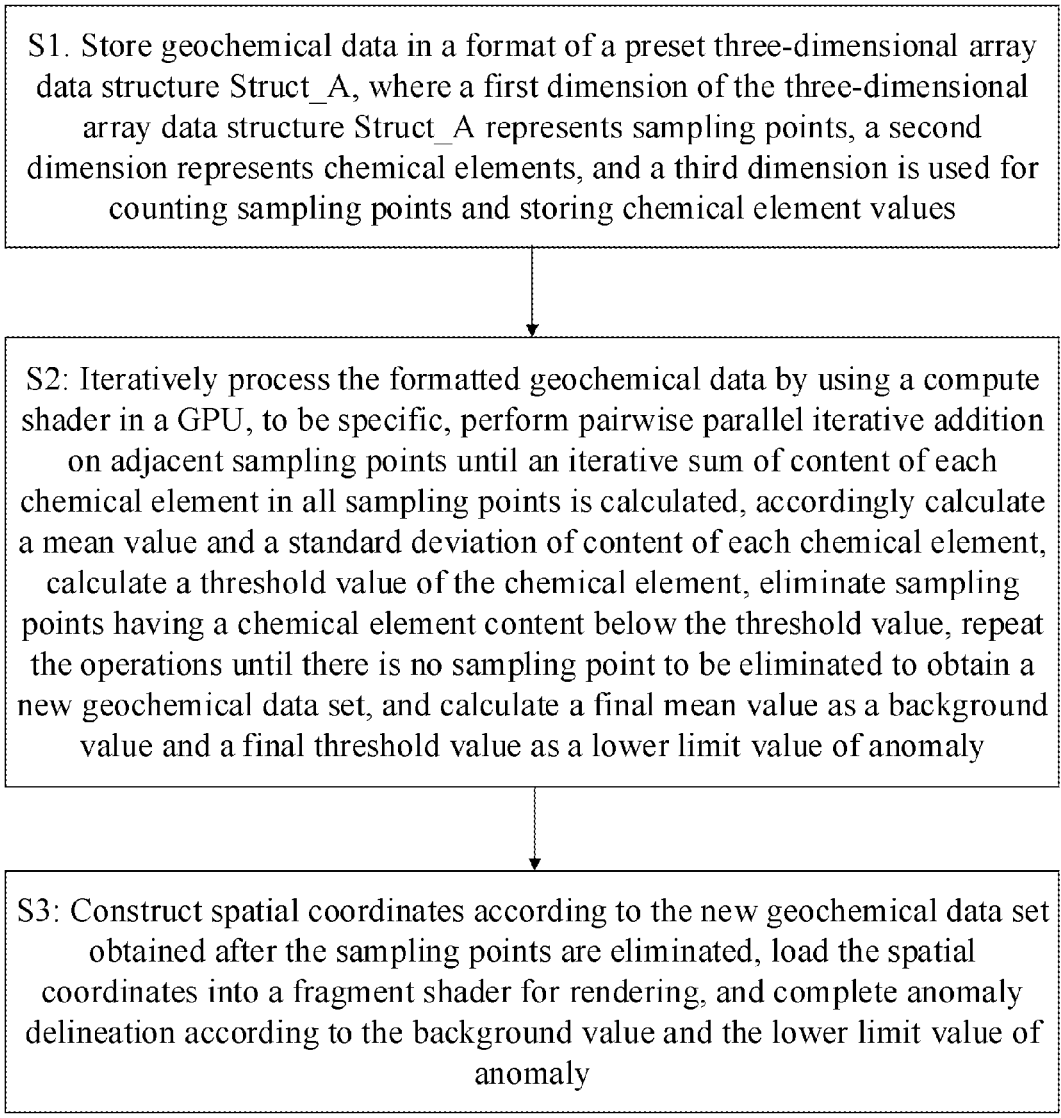
FIG. 1 is a schematic flowchart showing a GPU-based integrated processing method for geochemical data according to the present disclosure.

Referring to FIG. 1, the present disclosure provides a GPU-based integrated processing method for geochemical data.

The method includes three key steps: 1. conversion of geochemical data through construction of a three-dimensional data structure; 2. calculation of a background value and a lower limit of anomaly; and 3. anomaly delineation.

In step 1, a data structure Struct_A is defined. Struct_A is a three-dimensional array, a first dimension represents sampling points, a second dimension represents elements, and a third dimension only contains two values: C and V. C is an integer value for counting the sampling points, V is a floating-point value for storing chemical element values, and the size of the third dimension is fixed as S. Counting from 0, if a correlation value of an $m^{th}$ element in an $n^{th}$ sampling point is accessed, its offset in the data structure is $(S \times m)+(S \times m \times n)$.

Figure 2:
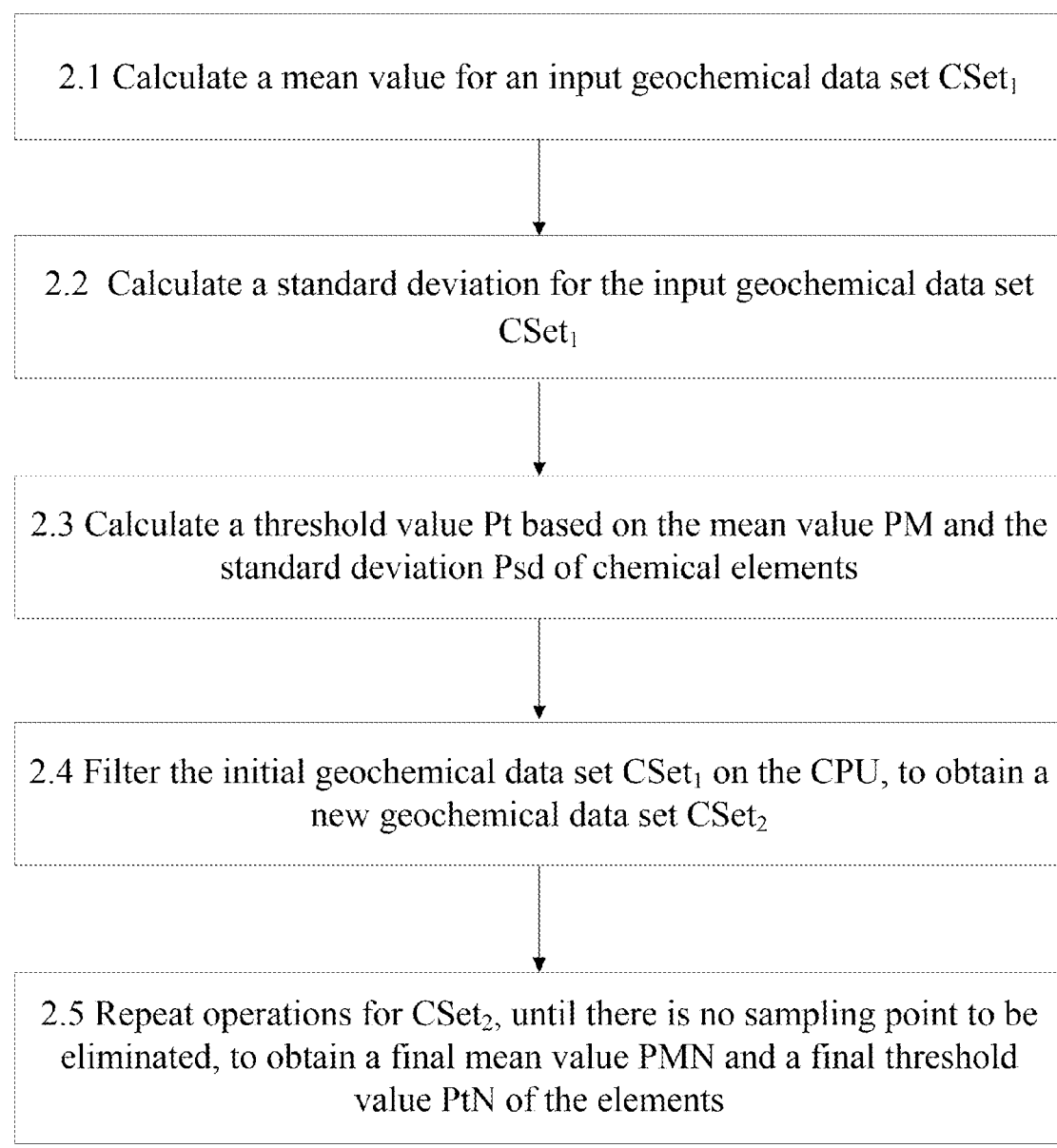
FIG. 2 is a schematic flowchart showing a step 2 in a GPU-based integrated processing method for geochemical data according to the present disclosure.
Figure 3:
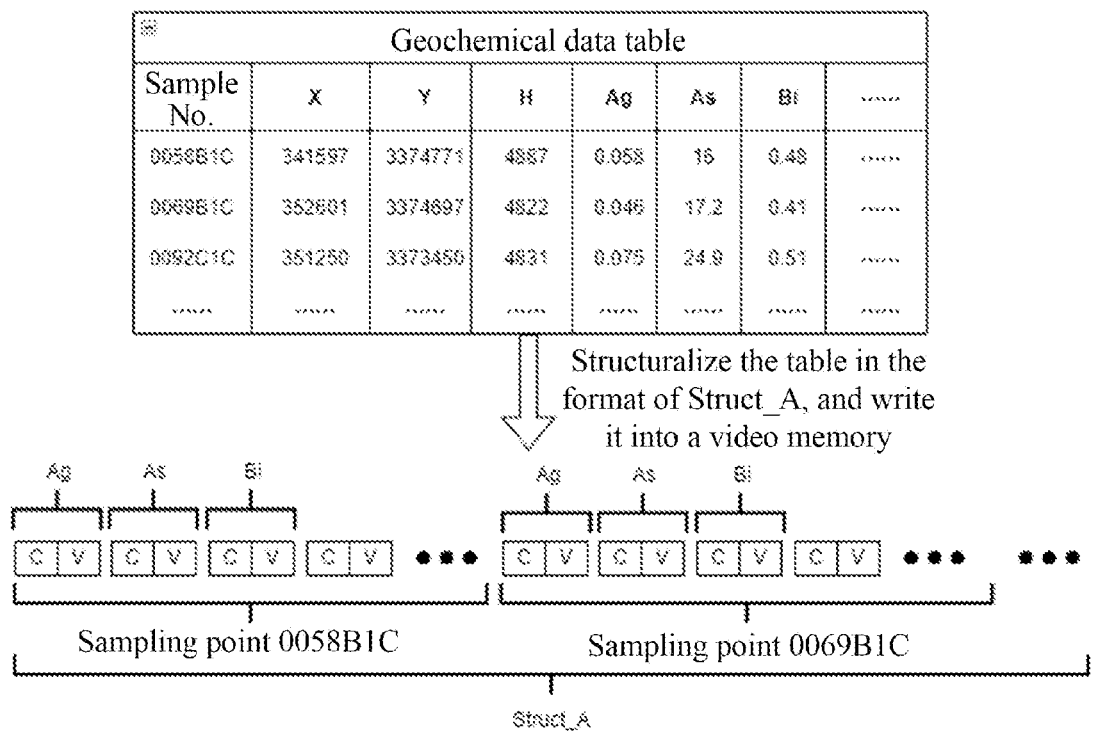
FIG. 3 is a schematic diagram of a data structure involved in steps 2.1.1 and 2.1.2 in a GPU-based integrated processing method for geochemical data according to the present disclosure.

In step 2, as shown in FIG. 2, the calculation of the background value primarily involves the utilization of a compute shader. An initial geochemical data set is denoted as $CSet_1$, and specific processing steps are as follows:

In 2.1, a mean value is calculated for the input geochemical data set $CSet_1$, and the specific method is as follows:

In 2.1.1, referring to FIG. 3, a buffer Buffer_1 in the format of Struct_A is created in the video memory, and Buffer_1 can be directly accessed by the compute shader and is used as a first input buffer of the compute shader. All values in the initial geochemical data set $CSet_1$ are written into Buffer_1, and C values of all chemical elements in the initial geochemical data set $CSet_1$ are initialized to 1.

In 2.1.2, a buffer Buffer_2 in the format of Struct_A is created in the video memory, and Buffer_2 can be directly accessed by the compute shader and is used as a first output buffer of the compute shader. Buffer_2 can store half the number of sampling points as Buffer_1. C values and V values of all the chemical elements in Buffer_2 are initialized to 0.

Figure 4:
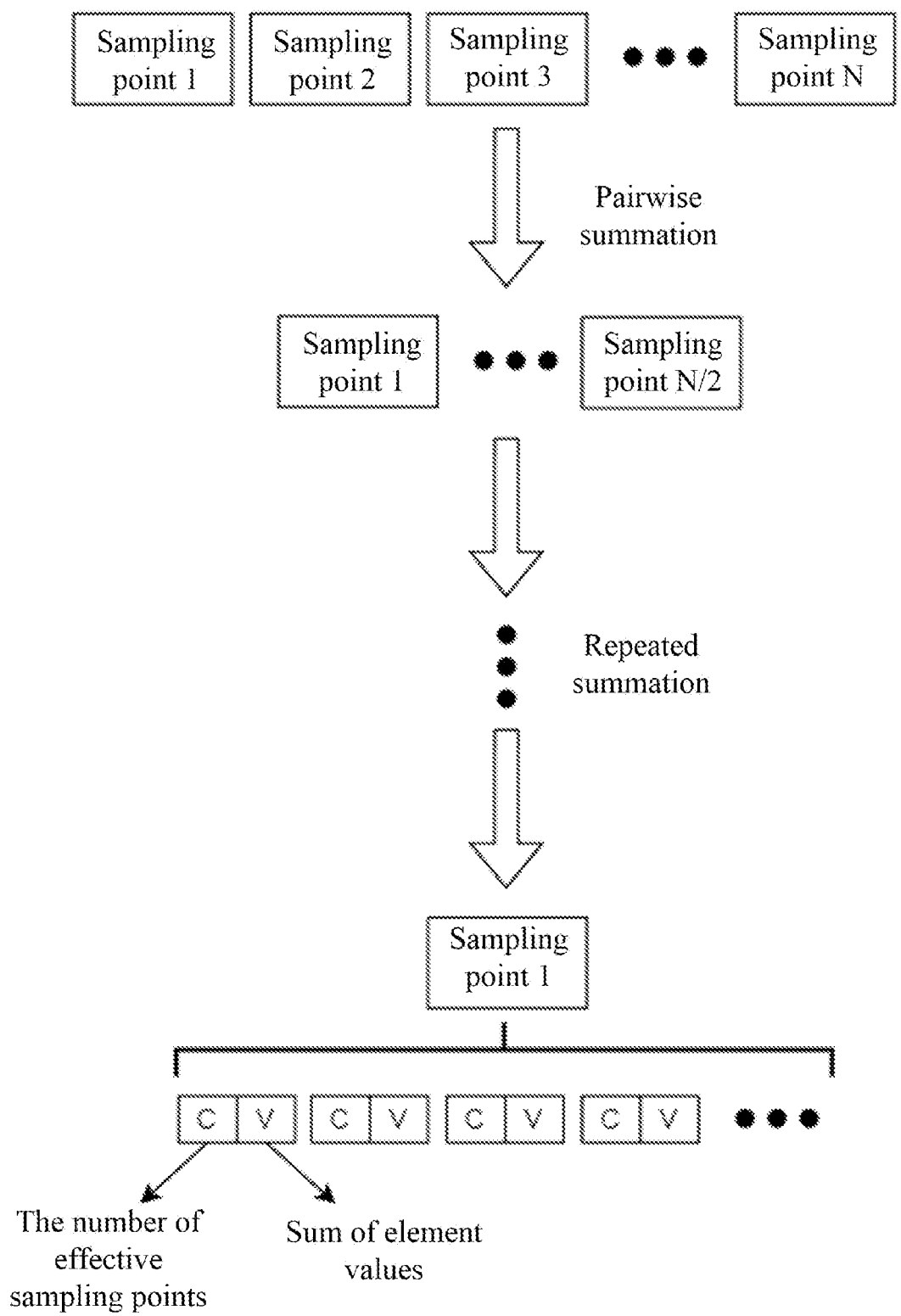
FIG. 4 is a schematic diagram of a data structure involved in steps 2.1.3 and 2.1.4 in a GPU-based integrated processing method for geochemical data according to the present disclosure.

In 2.1.3, referring to FIG. 4, a compute shader program is dispatched. The total number of threads dispatched is the number of sampling points in Buffer_2. The above compute shader program is dispatched as follows: The compute shader program determines a corresponding buffer offset by using a thread ID passed in by a main function. This offset is then used to locate the corresponding sampling point P1 in Buffer_1 and the adjacent sampling point P2 on its right. If a V value of an element in P1 or P2 is 0, a C value of the element is also set to 0. Then, vector summation is performed on the V values and C values in P1 and P2 to obtain a new sampling point PN, and the value of PN is written into Buffer_2. It should be noted that because the compute shader program takes two sampling points from Buffer_1 and writes one sampling point into Buffer_2, the size of Buffer_1 is twice that of Buffer_2, and the corresponding memory offset of Buffer_1 is twice that of Buffer_2.

In 2.1.4, parallel vector summation is performed again on C and V in adjacent sampling points stored in Buffer_2, that is, the steps 2.1.2 and 2.1.3 are repeated until there is only one sampling point output in Buffer_2. The C value of each chemical element in this sampling point is the number of effective sampling points for the element, and the V value denotes the sum of the element values across all the sampling points. C ⊘ V is calculated for the sampling point, that is, a mean value PM of the chemical element is obtained.

In the present disclosure, during the summation step prior to calculating the mean value, all sampling points' values are cyclically summed if on the CPU. For instance, when calculating a+b+c+d+e+f+g+h on the CPU, it is necessary to perform the addition as follows: first, calculate a+b, then add c, and subsequently add d. If each addition operation takes one clock cycle, this entire process would require seven clock cycles. After transitioning to GPU, this simple addition approach faces a limitation where each operation depends on the result of the previous operation. As a result, operation parallelization becomes unfeasible, and the full potential of GPU's multi-core advantage cannot be realized. Therefore, an algorithmic improvement is necessary. The task can be divided into separate calculations, such as a+b, c+d, e+f, and g+h. These four addition operations can be performed on four different GPU cores. This allows for obtaining four results in a single clock cycle. Then, the pairs of these results are added together iteratively until only one final result remains, representing the overall sum. By adopting this approach, it is possible to complete all operations in just three clock cycles. This represents a saving of more than half of the clock cycles compared to the sequential calculation method used on the CPU.

Figure 5:
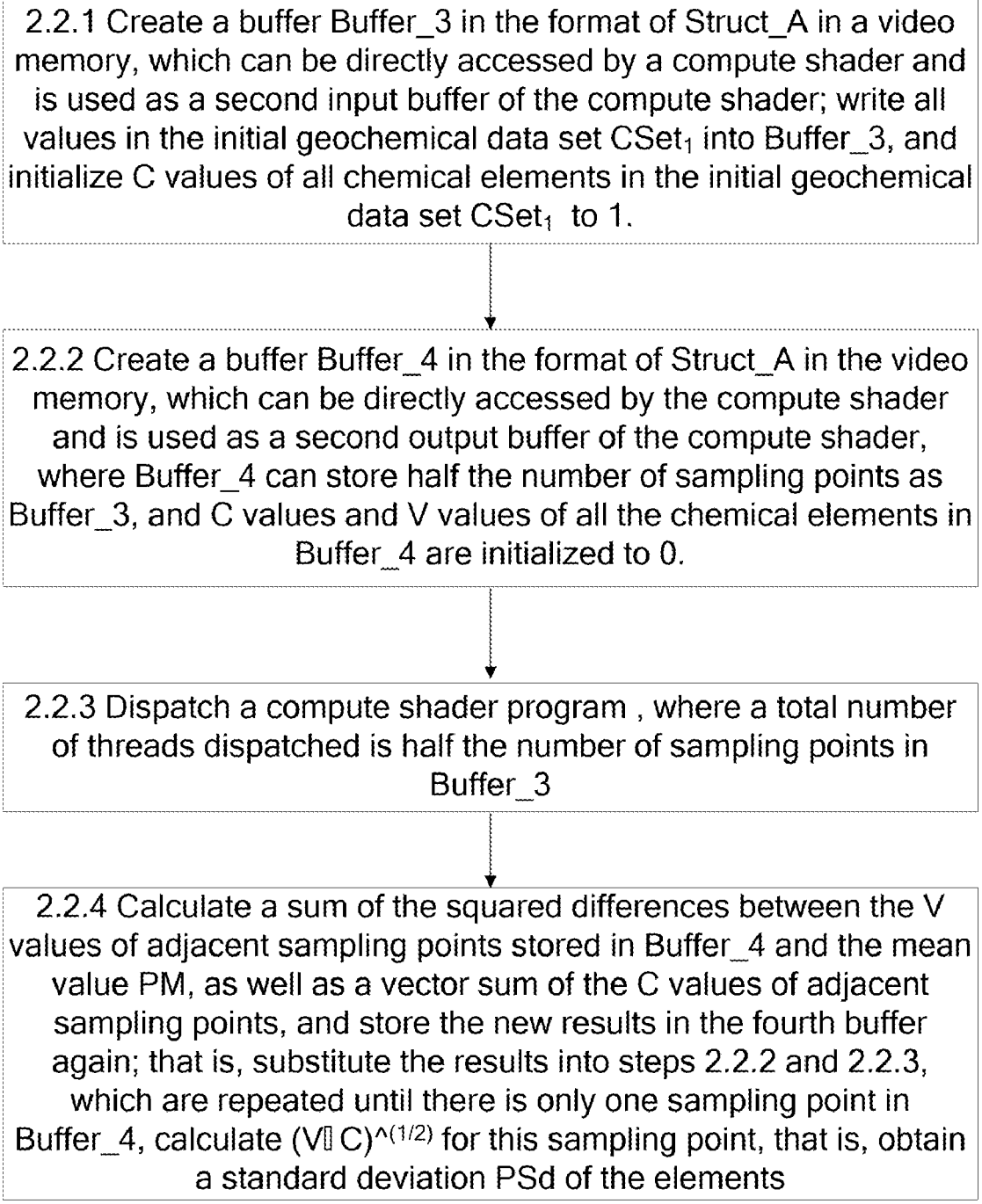
FIG. 5 is a schematic flowchart showing a step 2.2 in a GPU-based integrated processing method for geochemical data according to the present disclosure.

In 2.2, referring to FIG. 5, a standard deviation is calculated for the input geochemical data set $CSet_1$, and the specific processing steps are as follows:

In 2.2.1, a buffer Buffer_3 in the format of Struct_A is created in the video memory, and Buffer_3 can be directly accessed by the compute shader and is used as a second input buffer of the compute shader. All values in the initial geochemical data set $CSet_1$ are written into Buffer_3, and C values of all chemical elements in the initial geochemical data set $CSet_1$ are initialized to 1.

In 2.2.2, a buffer Buffer_4 in the format of Struct_A is created in the video memory, and Buffer_4 can be directly accessed by the compute shader and is used as a second output buffer of the compute shader. Buffer_4 can store half the number of sampling points as Buffer_3. C values and V values of all the chemical elements in Buffer_4 are initialized to 0.

In 2.2.3, a compute shader program is dispatched. The total number of threads dispatched is half the number of sampling points in Buffer_3. The above compute shader program is dispatched as follows: the compute shader program determines a corresponding memory offset by using a thread ID passed in by the main function, and obtains the mean value PM of each chemical element obtained in the step 2.1.4 through an external Uniform variable. The memory offset is used to locate the corresponding sampling point P1 in Buffer_3 and the sampling point P2 on its right. If a V value of a chemical element in P1 or P2 is 0, a C value of the chemical element is also set to 0. The V value is used for calculating $(P1 \ominus PM)^{\circ 2} \oplus (P2 \ominus PM)^{\circ 2}$ (vector subtraction is performed on V of P1 and PM, as well as V of P2 and PM, the obtained components are squared, and then vector summation is performed on the two resulting vectors). The C value is used to calculate $P1 \oplus P2$, to obtain the result PD, and write it into Buffer_4. When accessing Buffer_3 and Buffer_4, similarly, because the compute shader program takes two sampling points from Buffer_3 and writes one sampling point into Buffer_4, the size of Buffer_3 is twice that of Buffer_4, and the corresponding memory offset of Buffer_3 is twice that of Buffer_4.

In 2.2.4, the sum of the squared differences between the V values of adjacent sampling points stored in Buffer_4 and the mean value PM, as well as the vector sum of the C values of adjacent sampling points are calculated, and the new results are stored in the fourth buffer again. That is, the results are substituted into steps 2.2.2 and 2.2.3, which are repeated until there is only one sampling point in Buffer_4. $(V \oslash C)^{\circ 1/2}$ is calculated for this sampling point, that is, the standard deviation PSd of the elements is obtained.

In the actual implementation of the present disclosure, the data structure Struct_A is defined to accommodate the attributes of two fundamental processing operations in geochemical data processing. The essence of geochemical data processing involves a cycle of three steps: (1) calculating the mean value, (2) calculating the standard deviation, and (3) filtering. According to the attributes of these three operations, the data structure of Struct_A is adopted in the present disclosure. It can be seen that throughout the entire operation, the calculation for each step is realized by reusing the two variables C and V, without defining a dedicated storage mode for each operation, which simplifies the program design, and reduces the overhead of memory copying, thus improving the operation efficiency.

In 2.3, the threshold value $Pt=PM \oplus n \cdot PSd$ is calculated. n is taken according to the data processing requirements, and usually falls within [2,3]. This step can be completed in CPU because of its small amount of calculation.

In 2.4, the initial geochemical data $CSet_1$ is filtered on the CPU; if the value of an element is lower than its corresponding value in Pt, the value of the element is set to 0; or if the values of all elements in a sampling point are 0, the sampling point is excluded. After elimination, a new geochemical data set $CSet_2$ is obtained, containing $M_1$ sampling points and N elements.

In 2.5, the steps 2.1-2.4 are repeated for $CSet_2$ until there is no more sampling point to be eliminated in step 2.4, to obtain the final mean value PMN and the final threshold value PtN of the elements. PMN is the background value and PtN is the lower limit of anomaly.

In step 3, referring to FIG. 6, anomaly delineation mainly uses a fragment shader (or pixel shader). In this case, the geochemical data set is $CSet_2$, and each sampling point in $CSet_2$ contains spatial coordinates. The specific steps are as follows:

In 3.1, the data from $CSet_2$ is used to construct a Vertex. The spatial coordinates are used as vertex coordinates and the chemical element values are used as vertex attributes (GLSL attributes, or other equivalent methods).

In 3.2, $CSet_2$ is triangulated in any method, to generate a list of vertex numbers for triangle drawing. In this process, data interpolation can be performed to obtain a smoother anomaly map.

In 3.3, a fragment shader program is dispatched, and the background value PMN and the lower limit value PtN of anomaly obtained in step 2.5 are transmitted in a uniform form and the fragment shader program is dispatched. The fragment shader program is dispatched according to the following steps: In 3.3.1, the anomalous color of a chemical element is defined as C1 and the non-anomalous color as C2. For each pixel of the chemical element, if the value of the chemical element in the pixel attribute (GLSL varying or other equivalent methods) is greater than PMN or PtN, the pixel color is set as C1; otherwise, the pixel color is set as C2. In 3.3.2, the color mixing method for a multi-element anomaly map can be selected according to actual situations.

In 3.4, the anomaly delineation is completed.

Figure 7:
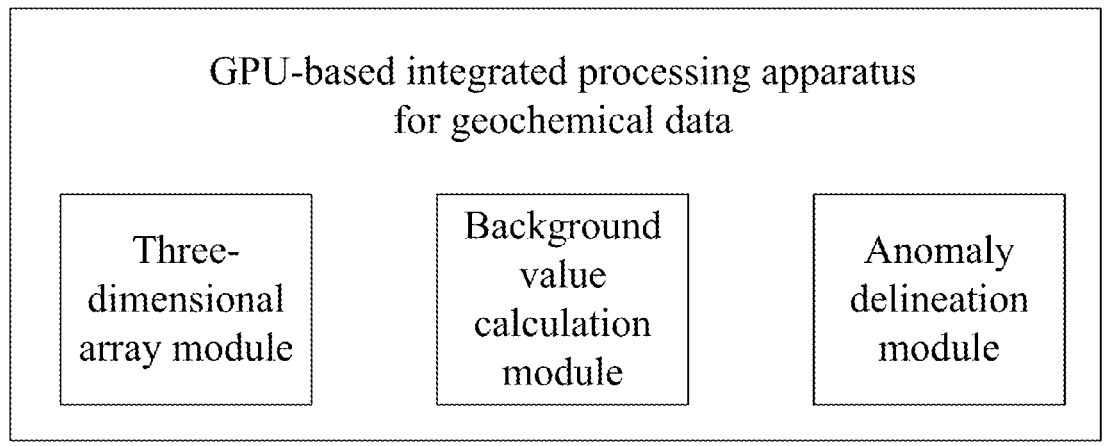
FIG. 7 is a schematic structural diagram showing a GPU-based integrated processing apparatus for geochemical data according to the present disclosure.

Referring to FIG. 7, a GPU-based integrated processing apparatus for geochemical data according to the present disclosure includes the following modules:

A three-dimensional array module is configured to define a three-dimensional array data structure Struct_A. A first dimension represents sampling points, a second dimension represents elements, and a third dimension only contains two values: C and V. C is an integer value for counting the sampling points, V is a floating-point value for storing chemical element values, and the size of the third dimension is fixed as S. Counting from 0, if a correlation value of an $m^{th}$ element of an $n^{th}$ sampling point is accessed, its offset in the data structure is $(S \times m) + (S \times m \times n)$.

A background value calculation module is configured to iteratively process the formatted geochemical data by using a compute shader in a GPU. To be specific, pairwise parallel iterative addition is performed on adjacent sampling points until an iterative sum of content of each chemical element in all sampling points is calculated, accordingly a mean value and a standard deviation of content of each chemical element are calculated, and a threshold value of the chemical element is calculated, sampling points having a chemical element content below the threshold value are eliminated, and the operations are repeated until there is no sampling point to be eliminated, to obtain a final mean value as a background value and a final threshold value as a lower limit value of anomaly.

An anomaly delineation module is configured to construct spatial coordinates according to a new geochemical data set obtained after the sampling points are eliminated, load the spatial coordinates into a fragment shader for rendering, and complete anomaly delineation according to the background value and the lower limit value of anomaly.

Figure 8:
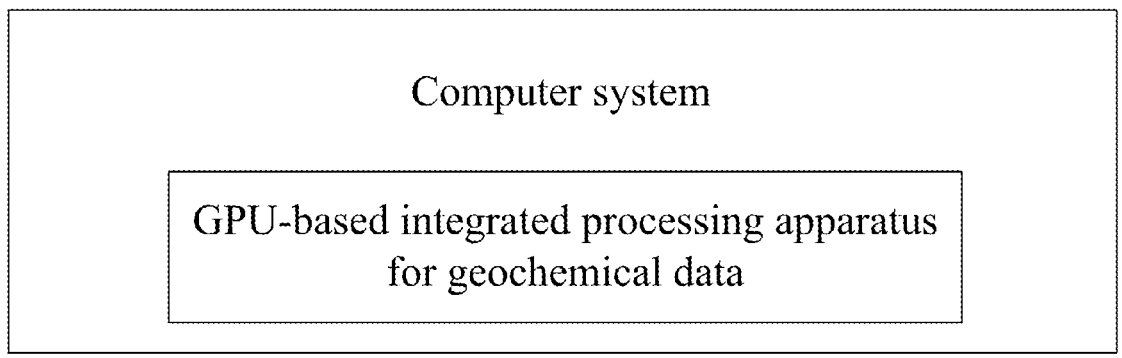
FIG. 8 is a schematic structural diagram showing a computer system according to the present disclosure.

Referring to FIG. 8, a computer system of the present disclosure includes a GPU-based integrated processing apparatus for geochemical data.

The application principles of the compute shader and the fragment shader in the present disclosure are as follows:

At present, mainstream parallel operations are commonly executed using CUDA. This is primarily due to NVIDIA's dominance in the market. However, CUDA is a proprietary standard of NVIDIA and not an industrial standard. Consequently, its hardware applicability is inherently limited. The most widely supported alternative to CUDA, which is essentially equivalent, is the compute shader. Compute shaders are an integral part of the OpenGL 4.6 standard and are supported by nearly all GPU manufacturers today.

The OpenGL 4.6 standard encompasses five types of shaders: the vertex shader, the tessellation shader, the geometry shader, the fragment shader, and the compute shader. Among these, only compute shaders are suited for general-purpose calculations, while the other shaders primarily serve image rendering purposes. Therefore, compute shaders are the preferred choice for data computation.

The anomaly delineation step in the present disclosure essentially involves coloring operations for pixels, which corresponds to the fragment shader in the OpenGL 4.6 standard in the pixel processing stage, making the fragment shader an appropriate choice for calculations.

The following description is made with a specific embodiment.

EMBODIMENT

Suppose processing geochemical data stored in the form of an Excel table, with a total of 16 elements, as shown in the following table:

| Detection No. | Password No. | Sample No. | X | Y | H | Ag | As | Bi | Cd | Co | ... |
|---|---|---|---|---|---|---|---|---|---|---|---|
| HT192030008 | 0002C3 | 0058B1C | 341597 | 3374771 | 4887 | 0.058 | 16 | 0.48 | 0.16 | 9.67 | ... |
| HT192030051 | 0014C1 | 0069B1C | 352601 | 3374697 | 4822 | 0.046 | 17.2 | 0.41 | 0.14 | 6.82 | ... |
| HT192030101 | 0031C3 | 0092C1C | 351250 | 3373450 | 4831 | 0.075 | 24.9 | 0.51 | 0.13 | 5.77 | ... |
| HT192030200 | 0059C1 | 0106A1C | 341284 | 3372594 | 4944 | 0.043 | 21.9 | 0.56 | 0.14 | 8.23 | ... |
| HT192030250 | 0075A2 | 0153B1C | 340634 | 3370596 | 4967 | 0.059 | 39.2 | 0.74 | 0.14 | 12.2 | ... |
| HT192030300 | 0088B2 | 0177C1C | 340340 | 3369252 | 5041 | 0.068 | 27.5 | 0.78 | 0.11 | 8.98 | ... |
| HT192030350 | 0101C1 | 0185C1C | 348144 | 3369151 | 4887 | 0.057 | 21.8 | 0.56 | 0.096 | 5.97 | ... |
| HT192030400 | 0113D2 | 0208C1C | 347064 | 3368459 | 4897 | 0.073 | 21.1 | 0.42 | 0.092 | 5.36 | ... |
| ... | ... | ... | ... | ... | ... | ... | ... | ... | ... | ... | ... |

Using OpenGL, Vulkan, or DirectX, the process is as follows:
1: The Excel table is read into the memory using any suitable method.
2: In Struct_A, the data format of C is uint32 and the data format of Vis float32
3: Buffer_1 is created in the video memory, and the data in the Excel table is written into the buffer line by line in the format of Struct_A.
4: Buffer_2 is created in the video memory, with a size that is half of Buffer_1.
5: A compute shader program is created to calculate the background value.
6: The compute shader program is loaded and compiled, Buffer_1 and Buffer_2 are bound to the program, and the compute shader program is dispatched, with the number of threads being the number of sampling points in Buffer_2.
7: After the dispatching is completed, Buffer_1 is discarded and Buffer_2 is rebound to Buffer_1, a new Buffer_2 is created and bound to the original Buffer_2 position in the compute shader, and the program is re-dispatched.
8: Step 7 is repeated until there is only one sampling point in Buffer_2. For each element, v_mean=target. V/target.C, that is, the background value.
9: Steps 3 and 4 are repeated.
10: A compute shader program is created to calculate the standard deviation.
11: The compute shader program is loaded and compiled, Buffer_1 and Buffer_2 are bound to the program, and the compute shader program is dispatched, with the number of threads being the number of sampling points in Buffer_2.
12: After the dispatching is completed, Buffer_1 is discarded and Buffer_2 is rebound to Buffer_1, a new Buffer_2 is created and bound to the original Buffer_2 position in the compute shader, and the program is re-dispatched.
13: Step 7 is repeated until there is only one sampling point in Buffer_2. For each element, v_sd=sqrt(target. V/target.C), that is, the standard deviation.
14: For each element, the background value is v_mean, and the lower limit of anomaly is pt=v_mean+3*v_sd.
15: A VBO is created using data from the Excel table.
16: A fragment shader program is created.
17: The fragment shader program is loaded and compiled, and the VBO containing geochemical data is bound. The fragment shader is used for rendering.
18: The anomaly delineation is completed.

The application further provides a computer-readable storage medium, such as a flash memory, a hard disk, a multimedia card, a card-type memory (for example, a SD or DX memory), a random access memory (RAM), a static random access memory (SRAM), a read-only memory (ROM), an electrically erasable programmable read-only memory (EEPROM), a programmable read-only memory (PROM), a magnetic memory, a magnetic disk, an optical disk, a server, an application. The storage medium stores a computer program. The program is executed by a processor to implement corresponding functions. The computer-readable storage medium of the embodiments is used to store a computer program. The computer program is executed by a processor to implement the GPU-based integrated processing method for geochemical data according to the method embodiments.

The present disclosure focuses on enhancing the traditional geochemical data processing method known as the "iteration method" by leveraging compute shaders. The geochemical data processing workflow involves calculating the mean value, calculating the standard deviation, and filtering the sample geochemical data through iterative steps, to determine regional geochemical background value and lower limit of anomaly, which are used to distinguish which samples are "anomalous values", ultimately aiding in the delineation of potential prospecting regions. The present disclosure is based on the core concept of the iterative method, and the process is divided into steps such as calculating the mean value, calculating the standard deviation, and filtering. Based on the traditional calculation method, the present disclosure adapts parallel processing, to achieve the same results on the GPU as on the CPU and improve the processing speed.

To sum up, the present disclosure greatly improves the efficiency of geochemical data processing and anomaly delineation, and enables users to process geochemical data in near real time. In comparative experiments, skilled users take approximately five minutes to process a total of 50,000 pieces of geochemical data of 16 elements, using traditional geochemical data processing software. Additionally, it takes around one minute to adjust the parameters for reprocessing. However, with the processing software of the present disclosure, even unskilled users can complete the anomaly delineation in just 10 seconds. Moreover, adjusting the parameters and reprocessing can be accomplished in mere one second. Compared with the prior art, the present disclosure demonstrates a qualitative improvement in user satisfaction.

It will be apparent to those skilled in the art that various modifications and variations can be made to the present disclosure without departing from the spirit and scope of the present disclosure. Thus, provided that these modifications and variations of the present disclosure fall within the scope of the claims of the present disclosure and their equivalents, the present disclosure will also be intended to include these modifications and variations.

The content not described in detail in the description belongs to the prior art well known to those skilled in the art.

What is claimed is:
1. A graphics processing unit (GPU)-based integrated processing method for geochemical data, comprising:
S1: storing geochemical data in a format of a preset three-dimensional array data structure Struct_A, wherein a first dimension of the three-dimensional array data structure Struct_A represents sampling points, a second dimension represents chemical elements, and a third dimension is used for counting sampling points and storing chemical element values;
S2: iteratively processing the formatted geochemical data by using a compute shader in a GPU, to be specific, performing pairwise parallel iterative addition on adjacent sampling points until an iterative sum of content of each chemical element in all sampling points is calculated, accordingly calculating a mean value and a standard deviation of content of each chemical element, calculating a threshold value of the chemical element, eliminating sampling points having a chemical element content below the threshold value, repeating the operations until there is no sampling point to be eliminated to obtain a new geochemical data set, and calculating a final mean value of the new geochemical data set as a background value and a final threshold value of the new geochemical data set as a lower limit value of anomaly; and S3: constructing spatial coordinates according to the new geochemical data set, loading the spatial coordinates into a fragment shader for rendering, and completing anomaly delineation according to the background value and the lower limit value of anomaly;

wherein the step S3 specifically comprises:

S31: creating a vertex buffer object (VBO) based on the new geochemical data set, wherein the spatial coordinates are used as vertex coordinates and the chemical element values are used as vertex attributes;

S32: triangulating the new geochemical data set, generating a list of vertex numbers for triangle drawing, and performing data interpolating in the process to obtain a smooth anomaly map to be delineated; and S33: according to the background value and the lower limit value of anomaly, coloring the anomaly map to be delineated in the fragment shader; when an attribute value of a vertex is greater than the background value or the lower limit value of anomaly, setting a pixel of the vertex as an anomalous color; otherwise, setting the pixel as a non-anomalous color, to complete the anomaly delineation.

2. The GPU-based integrated processing method for geochemical data according to claim 1, wherein the step S2 specifically comprises:

S21: creating a first buffer and a second buffer accessible to the compute shader, writing an initial geochemical data set CSeti in the format Struct_A into the first buffer, performing pairwise parallel vector summation on sampling point count values C and chemical element values V of adjacent sampling points, storing results in the second buffer, performing pairwise summation on data in the second buffer and storing results in the first buffer, repeating the operations until a vector sum of the sampling point count values C and the chemical element values V of all the chemical elements in all the sampling points is calculated, and calculating a mean value PM of each chemical element by determining a ratio of the C to the V;

S22: creating a third buffer and a fourth buffer accessible to the compute shader, writing the initial geochemical data set $CSet_1$ into the third buffer, parallelly calculating a sum of squared differences between the chemical element values V of each chemical element and the corresponding mean value PM in adjacent sampling points and calculating a vector sum of the sampling point count values C in adjacent sampling points, storing results in the fourth buffer, performing pairwise parallel summation on adjacent sampling points in the fourth buffer and storing results in the third buffer, repeating the operations until a sum of squared differences between the chemical element values V and the mean value PM and a vector sum of the sampling point count values C in all sampling points are calculated, and accordingly calculating a standard deviation PSd of each chemical element; calculating the threshold value according to the mean value PM and the standard deviation PSd, and filtering the initial geochemical data set $CSet_1$ according to the threshold value to obtain a filtered geochemical data set $CSet_2$; and S23: filtering the filtered geochemical data set $CSet_2$ in a same manner until there is no sampling point to be eliminated; and obtaining the final mean value PMN of each chemical element as the background value, and the final threshold value PtN of each chemical element as the lower limit value of anomaly.

3. The GPU-based integrated processing method for geochemical data according to claim 2, wherein the sampling point count values C of all chemical elements in the initial geochemical data set $CSet_1$ are initialized to 1; and the sampling point count values C and the chemical element values V of all chemical elements in the second buffer and the fourth buffer are initialized to 0.

4. The GPU-based integrated processing method for geochemical data according to claim 2, wherein a memory offset of the first buffer is twice of a memory offset of the second buffer.

5. The GPU-based integrated processing method for geochemical data according to claim 2, wherein a memory offset of the third buffer is twice of a memory offset of the fourth buffer.

6. The GPU-based integrated processing method for geochemical data according to claim 2, wherein when a chemical element value of a chemical element in adjacent sampling points is 0, a sampling point count value of the chemical element is also set to 0.

7. The GPU-based integrated processing method for geochemical data according to claim 1, wherein when the anomaly map to be delineated is a multi-chemical element anomaly map, multiple color mixing methods are selected according to actual situations.

8. A GPU-based integrated processing apparatus for geochemical data, wherein the apparatus comprises:

a three-dimensional array module configured to store geochemical data in a format of a preset three-dimensional array data structure Struct_A, wherein a first dimension of the three-dimensional array data structure Struct_A represents sampling points, a second dimension represents chemical elements, and a third dimension is used for counting sampling points and storing chemical element values;

a background value calculation module configured to iteratively process the formatted geochemical data by using a compute shader in a GPU, to be specific, perform pairwise parallel iterative addition on adjacent sampling points until an iterative sum of content of each chemical element in all sampling points is calculated, accordingly calculate a mean value and a standard deviation of content of each chemical element, calculate a threshold value of the chemical element, eliminate sampling points having a chemical element content below the threshold value, repeat the operations until there is no sampling point to be eliminated to obtain a new geochemical data set, and calculate a final mean value of the new geochemical data set as a background value and a final threshold value of the new geochemical data set as a lower limit value of anomaly; and an anomaly delineation module configured to construct spatial coordinates according to the new geochemical data set, load the spatial coordinates into a fragment shader for rendering, and complete anomaly delineation according to the background value and the lower limit value of anomaly; the anomaly delineation module has been specifically used to creating a vertex buffer object (VBO) based on the new geochemical data set, wherein the spatial coordinates are used as vertex coordinates and the chemical element values are used as vertex attributes; triangulating the new geochemical data set, generating a list of vertex numbers for triangle drawing, and performing data interpolating in the process to obtain a smooth anomaly map to be delineated;

according to the background value and the lower limit value of anomaly, coloring the anomaly map to be delineated in the fragment shader; when an attribute value of a vertex is greater than the background value or the lower limit value of anomaly, setting a pixel of the vertex as an anomalous color; otherwise, setting the pixel as a non-anomalous color, to complete the anomaly delineation.

* * * * *